(12) United States Patent
Carratelli

(10) Patent No.: US 6,355,489 B1
(45) Date of Patent: Mar. 12, 2002

(54) METHOD FOR THE DETERMINATION OF OXYGEN-CENTERED FREE RADICALS

(75) Inventor: Mauro Carratelli, Grosseto (IT)

(73) Assignee: Diacron S.r.l., Grosseto (IT)

( * ) Notice: Subject to any disclaimer, the term of this patent is extended or adjusted under 35 U.S.C. 154(b) by 0 days.

(21) Appl. No.: 09/332,513

(22) Filed: Jun. 14, 1999

Related U.S. Application Data

(63) Continuation-in-part of application No. 08/809,832, filed on Mar. 21, 1997, now abandoned.

(51) Int. Cl.[7] ............................................. G01N 21/75
(52) U.S. Cl. ........................ 436/164; 436/124; 436/166
(58) Field of Search ................................ 436/164, 166, 436/124, 125

(56) References Cited

U.S. PATENT DOCUMENTS

| | | | | |
|---|---|---|---|---|
| 4,886,760 A | 12/1989 | Ben-Michael | ................ | 436/66 |
| 5,362,650 A | 11/1994 | Harp | .......................... | 436/125 |

FOREIGN PATENT DOCUMENTS

| | | |
|---|---|---|
| DE | 2502467 | 7/1976 |
| DE | 135243 | 4/1979 |
| DE | 3114935 | 11/1982 |
| GB | 813493 | 5/1959 |
| JP | 50-75492 | 6/1975 |

OTHER PUBLICATIONS

A. T. Palin, et al. Methoden zur Bestimmung des im Wasser vorhandenen freien und gebundenen wirksamen Cholrs, Chlordioxids und Chlorits, Broms, Jods, und Ozons unter Verwendung von Diäthyl–p–Phenylen–diamin (DPD), *Vom Wasser*, vol. 40, 1973 Berlin, pp. 151–163.
Database WPI, Section Ch, Week 9143, Derwent Publications Ltd., London, GB; Class A89, AN 91–315139 & JP,A,03 211 460 (Yonjun K.), Sep. 17, 1991.
V. Pchelin, Chem. Abstr., 1937, 31, 32835.
E. Abrantes et al., Chem. Abstr., 1938, 32, 32893.
L. Michaelis et al., J. Am. Chem. Soc., 1939, 61, 1981–1992.
L. Michaelis et al., J. Am. Chem. Soc., 1943, 65, 1747–1755.
L. M. Kul'berg et al. Chem. Abstr. 1954, 48, 869ld.
E F. Ruth, Chem. Abstr., 1955, 49, 5210 i.
D. F. Kuemmel et al. Anal Chem., 1956, 28, 1674–1678.
P.R. Dugan, Anal. Chem., 1961, 33, 696–697.
P.R. Dugan, Anal. Chem., 1963, 35, 414–415.
D. J. Gupta et al., Z. Anal. Chem., 1971, 257, 275–277.
D. J. Leggett et al., Fresemius Z. Anal. Chem . . . , 1983, 315, 47–50.
D. Armstrong et al., Chem. Abstr., 1984, 100, 19638u.
J. C. Thompsen et al., Z. Anal. Chem., 1984, 56, 2834–2836.
E. M. Sevast'yanova et al., Chem. Abstr., 1987, 106, 143701x.
V. Pchelin, J. Applied Chem. (USSR), 1936, 9, 846–854.
E. Abrantes et al., Rev. Soc. Brasilquim, 1937, 6, 153–159.
M.J. Sienko et al., "Chemical Principles and Properties". McGraw–Hill, Inc., New York, 1974, pp. 655–659.
P.S. Rao et al., J. Phys. Chem., 1975, 79, 397–402.
P.S. Rao et al., J. Phys. Chem., 1975, 79, 1063–1066.
S. Fujita et al., J. Am. Chem. Soc., 1981, 103, 2540–2545.
D. K. Hazra et al., J. Am. Chem. Soc., 1983, 105, 4380–4386.
E. M. Sevast'yanova et al., Gig. Sanit, 1987, 48–49.
U. Nickel et al., Z. Phys. Chem. (Munich), 1991, 170, 159–183.
A.J.S.C. Vieira et al., J. Phys. Chem., 1991, 95, 9340–9346.
P. Aravindan et al., Int. J. Phys. Chem. Kinet 1995, 27, 102–122.

*Primary Examiner*—Lyle A. Alexander
(74) *Attorney, Agent, or Firm*—Smith Gambrell & Russell LLP

(57) ABSTRACT

The present invention relates to a method for determining the concentration of oxygen-centered free radicals in a sample. The method uses a chromogen chosen from the following group:

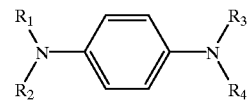

with $R_1$, $R_2$, $R_3$, and $R_4$ being —$CH_2CH_3$, —$CH_3$, —H, or —X, with X being a halogen. The method includes combining a working reagent having a selected chromogen and a buffer with a sample containing free radicals. Quantitative determination of the concentration of the free radicals in the sample is then determined, based on the chromogenic reaction which takes place.

21 Claims, No Drawings

METHOD FOR THE DETERMINATION OF OXYGEN-CENTERED FREE RADICALS

This application is a continuation-in-part of U.S. patent application Ser. No. 08/809,832, filed Mar. 21, 1997 now abandoned which is incorporated herein by reference in its entirety.

The present invention relates to a method for the determination of free radicals through the quantification of their quenching products. More particularly, the invention relates to a method which allows the determination of free radicals in any kind of clinical chemistry analyzer, such determination being possible in any laboratory having commonly available standard instrumentation.

As is well known to those skilled in the art, the term "free radical" is meant in the literature to include a chemical species able to exist independently and containing one or more unpaired electrons in the outermost atomic and/or molecular orbital.

Of the existing free radicals, those referred to as "oxygen-centered free radicals" (or more simply "oxygen-centered radicals") have attracted increasing interest in recent years in the medical field in view of the role they can assume for determination of tissue damage of different pathological conditions.

It should be pointed out that carbon centered radicals R· formed under aerobic conditions are quickly converted by oxygen to peroxy radicals ROO· which under reaction conditions are converted to hydroperoxides ROOH through hydrogen abstraction or, via dimerisation, to tetra-oxides ROOOOR, which in turn quickly fragment to alkoxy radicals RO· and oxygen.

Characteristic of these oxygen-centered radicals is to have an odd number of electrons in the oxygen outermost orbit, which makes them very reactive toward a great number of biologically relevant molecules.

In English language clinical medical literature, these radicals, the diamagnetic species originating from them, as well as their metabolites, are commonly called ROMs (Reactive Oxygen Metabolites). The main ROMs include the oxygen superoxide radical anion ($O_2^{-\cdot}$), alkoxy radicals (RO·), peroxy radicals (ROO·), hydroxy radical (HO·), hydrogen peroxide ($H_2O_2$), and hydroperoxides (ROOH).

Recent studies have indicated several clinical conditions where the ROMs are invoked or recognized to play a major role. In particular, these include inflammatory and post-ischemia diseases of the alimentary tract, central nervous system alterations resulting from vascular or traumatic disorders, atherosclerosis and its cardiac complications, some renal disorders, rheumatoid and deformans arthritis, and alcohol-induced disorders in specific parts of the organism. Under physiological conditions, free radicals are extremely labile (short-lived) and remain elusive species that cannot be detected, let alone quantified. Thus their pathogenic role in the above diseases has been deduced only by following the effects exerted by added antioxidants which could not have a specific anti-inflammatory activity of their own.

Even Electron Spin Resonance spectroscopy, which is the technique of choice for the direct detection and characterization of free radicals, is not normally successful in biological systems. Because this technique requires extremely sophisticated and expensive instruments, it cannot be adopted by diagnostic (analytic) laboratories for daily routine determinations.

This makes extremely important the herein defined simple methodology (protocol) based on the use of the present invention for the determination of free radicals and of their derivatives in samples of different natures, and especially in biological samples where the invention would allow the monitoring of the effects of antioxidant and anti-inflammatory therapies through analysis that can be carried out in any standard laboratory.

The applicant has been able to determine on an experimental basis that N, N-diethyl-para-phenylenediamine [$(C_2H_5)_2NC_6H_4NH_2$], hereafter indicated as chromogen, when used in an appropriate concentration in a buffer of suitable pH where a biological sample has been previously dissolved, undergoes a chromogenic reaction making it possible to determine the free radicals initially present in the biological sample through the hydroperoxides resulting from their quenching.

The red color developed in the chromogenic reaction is characterized by absorption peaks at 510 nm and 550 nm, as can be noted in graph 1, and perfectly follows the Lambert and Beers law at both wavelengths, as evidenced in the enclosed graph 2.

The invention is based on the fact that, as already mentioned, the free radicals formed in a biological system are eventually converted to hydroperoxides. When the biological sample is dissolved in the acidic buffer, the hydroperoxides are converted to alkoxy and peroxy radicals by the metal ions released by the proteins. These radicals receive an electron from the added chromogen which is therefore converted to the corresponding radical cation responsible for the red color.

If the sample is not of biological origin, the method must be modified by adding a third reagent (C), in particular a transition-metal ion salt, preferably an Iron (II) salt, in order to provide the transition-metal ions necessary to bring about the degradation of the hydroperoxides. It should be emphasized that in either case the presence of EDTA or other agents known to complex transition metal ions in the examined solution must be absolutely avoided, because it would inhibit the degradation of hydroperoxides.

The ROMs determination in blood, serum, liquor, etc. by the method of this invention can be made either by reading the absorbance (at 505 or 550 nm) when the color is fully developed (End Point reading), or by determining the rate of variation of the color in a predetermined time interval (Fixed Point reading).

The great advantage of this method over those presently known is that it does not require special apparatuses and can be used with the instrumentation already present in any laboratory.

The fact that the method proposed by the Applicant and using the method according to the invention requires the use of two separated reagents A and B, where A represents the chromogen and B a suitably buffered solution, is not a limitation: the two reagents are mixed in an appropriate proportion to make a sole working reagent. When reagent C is necessary, it should be added to the final buffer solution resulting from the mixing of A and B and already containing the sample to be examined.

It is therefore a specific object of the present invention to present a method for the determination of ROMs comprising a chromogen chosen from the following group:

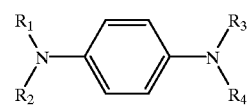

where $R_1$, $R_2$, $R_3$, and $R_4$=$CH_2CH_3$, $CH_3$, H, or X, with X being a halogen atom, the chromogen (A) being dissolved in water or other suitable solvent, and a buffer (B) having a pH value in the range 3 to 6.9.

Preferably, the chromogen and the buffer are mixed with a proportion between 1:20 and 1:300.

According to a first preferred embodiment of the invention, the chromogen comprises N, N-diethyl-para-phenylenediamine.

In a second preferred embodiment of the method according to the invention, the chromogen can comprise N, N-diethyl-paraphenylenediamine sulfate, $[C_{10}H_{16}N_2 \times H_2SO_4]$.

Still according to the invention, in a third preferred embodiment, said chromogen can comprise N, N-diethyl-para-phenylenediamine oxalate, $[C_{10}H_{16}N_2 \times C_2H_2O_4]$.

Further according to the invention, said chromogen can comprise N, N-dimethyl-para-phenylenediamine $[C_8H_{12}N_2]$, N, Ndimethyl-para-phenylendiamine sulfate, $[C_8H_{12}N_2 \times H_2SO_4]$, or N, Ndimethyl-para-phenylenediamine oxalate, $[C_8H_{12}N_2 \times C_2H_2O_4]$.

Preferably, according to the invention, said buffer (reagent B) will have a pH value between 4 and 5.

According to a preferred embodiment of the method according to the invention, a third reagent (C) is added, in particular a transition metal ion salt, preferably an Iron (II) salt in order to provide the transition-metal ions necessary to bring about the degradation of the hydroperoxides.

Preferably, said reagent C will be an aqueous solution of Iron (II) sulfate.

Furthermore, said reagent C shall be an aqueous solution of cuprous (I) salt, preferably cuprous sulfate.

A few example preparations of the reagents follow, but these must not be considered as limiting the scope of the invention, being only selected examples of the many possible preparations. In addition, it should be stressed that the shown ratios between chromogen and buffer can be modified according to the solubility of the former into the latter.

REAGENT A- Chromogen

Example A

Components: Dose relevant to 1,000 ml of A:

| | |
|---|---|
| N,N-diethyl-para-phenylenediamine | 1–200 gr |
| $H_2O$ | up to 1,000 ml |

Example B

| | |
|---|---|
| N,N-diethyl-para-phenylenediamine | 1–150 gr |
| $CH_3COOH$ | up to 1,000 ml |

Example C

| | |
|---|---|
| N,N-diethyl-para-phenylenediamine oxalate | 1–190 gr |
| $H_2O$ bidistilled | up to 1,000 ml |

REAGENT B - Buffer

Example 1 (can be used with chromogen preparation as in examples A and C)

| | |
|---|---|
| Acetate buffer | between pH 3 and pH 6.9 |

Example 2 (can be used with chromogen preparation as in example B)

| | |
|---|---|
| Sodium hydroxide | from 0.001 N to 1 N |

Example 3 (can be used with chromogen preparation as in examples A and B)

| | |
|---|---|
| Phosphate buffer | between pH 3 and pH 6.9 |

Example 4 (can be used with chromogen preparation as in examples A and B)

| | |
|---|---|
| Pipes buffer | between pH 3 and pH 6.9 |

Example 5 (can be used with chromogen preparation as in examples A and B)

| | |
|---|---|
| Epes buffer | between pH 3 and pH 6.9 |

REAGENT C - Transition metal salt solution

Example α (can be used with chromogen preparation as in examples A and B and buffer preparations as in examples 1–5)

| | |
|---|---|
| $FeSO_4 \times 7H_2O$ | 0.050–0.0152 gr |
| $H_2O$ | up to 1,000 ml |

Example β (can be used with chromogen preparation as in examples A and B and buffer preparations as in examples 1–5)

| | |
|---|---|
| $(CH_3CO_2)_2Fe$ | 0.0017–0.0052 gr |
| $H_2O$ | up to 1,000 ml |

Example γ (can be used with chromogen preparation as in examples A and B and buffer preparations as in examples 1–5)

| | |
|---|---|
| CuCl | 0.010–0.0030 gr |
| $H_2O$ | up to 1,000 ml |

Example δ (can be used with chromogen preparation as in examples A and B and buffer preparations as in examples 1–5)

| | |
|---|---|
| $CH_3CO_2Cu$ | 0.0012–0.0036 gr |
| $H_2O$ | up to 1,000 ml |

Working Reagent Preparation

Reagent A and reagent B are mixed together in a ratio 1:100 to 1:300, preferably 1:200.

For preparations following Example B the preferred ratio is 1:40.

End Point Method for Biological Samples (Blood, Serum, Liquor, etc,)

5 μl of biological sample are added to 1 ml of working reagent (A+B) and the resulting solution is thermostatted at +37° C. for 1.5 hours. The absorbance reading is carried out between 480 to 570 nm (preferably 505 nm). The test is executed in parallel with a sample of known concentration and applying the classic formula:

$$C_{sample} = (A_{sample}/A_{standard}) \times C_{standard}$$

End Point Method for Non-biological Samples

30 μl of the sample are added to 1 ml of working reagent (A+B). 30 μl of Reagent C are further added, and the resulting solution is thermostatted at +37° C. for 1.5 hours. The absorbance reading is carried out between 480 to 570 nm (preferably 505 mn). The test is executed in parallel with a sample of known concentration and applying the classic formula:

$$C_{sample} = (A_{sample}/A_{standard}) \times C_{standard}$$

Fixed Point Method for Biological Samples (Blood, Serum, Liquor, etc,)

20 μl of thermostatted sample are added to 1 ml of working reagent (A+B), thermostatted at +37° C., and the absorbance is read in the interval 480 to 570 nm (preferably 505 nm). The first reading is carried out after 30 seconds from mixing and the second reading after a 5 minute incubation. The following formula is then applied:

$$C_{sample} = \frac{\left(A_{sample}^{final} - A_{sample}^{initial}\right)}{\left(A_{standard}^{final} - A_{standard}^{initial}\right)} \times C_{standard}$$

Fixed Point Method for Non-biological Samples

20 μl of thermostatted sample are added to 1 ml of working reagent (A+B), thermostatted at +37° C. 20 μl of thermostatted reagent C are further added and the absorbance is read in the interval 480 to 570 nm (preferably 505 nm). The first reading is carried out after 30 seconds from mixing and the second reading after a 5 minute incubation. The following formula is then applied:

$$C_{sample} = \frac{\left(A_{sample}^{final} - A_{sample}^{initial}\right)}{\left(A_{standard}^{final} - A_{standard}^{initial}\right)} \times C_{standard}$$

Continuous Kinetics Method for Biological Samples (Blood, Serum, Liquor, etc,)

The preferred reaction temperature is +37° C., but the test can also be run at different temperatures.

10 μl of thermostatted sample are added to 1 ml of working reagent (A+B), thermostatted at +37° C., and the absorbance is read in the interval 480 to 570 nm (preferably 505 nm) at 1 minute intervals starting after 60 seconds from mixing. In the first minutes the rate of formation of the cation (the rate of variation of the optical density) is fairly constant and the following formula can be applied:

$$C_{sample} = \frac{\Delta A_{sample}}{\Delta A_{standard}} \times C_{standard}$$

where $\Delta A_{sample}$ and $\Delta A_{standard}$ are the variation of the optical density of the sample and standard solution in a 1 minute interval.

Continuous Kinetics Method for Non-biological Samples

The preferred reaction temperature is +37° C., but the test can also be run at different temperatures.

10 μl of thermostatted sample are , added to 1 ml of working reagent (A+B), thermostatted at +37° C.: 10 ml of thermostatted reagent C are further added and the absorbance is read in the interval 480 to 570 nm (preferably 505 mn) at 1 minute intervals starting after 60 seconds from mixing. In the first minutes the rate of formation of the cation (the rate of variation of the optical density) is fairly constant and the following formula can be applied:

$$C_{sample} = \frac{\Delta A_{sample}}{\Delta A_{standard}} \times C_{standard}$$

where $\Delta A_{sample}$ and $\Delta A_{standard}$ are the variation of the optical density of the sample and standard solution, respectively, in a 1 minute interval.

The above methods have been described for purposes of illustration, and by no means should they be considered to limit the invention. It is indeed to be understood that modifications and/or changes can be introduced by those skilled in the art without departing from the relevant scope as defined in the claims which follow.

I claim:

1. A method for determining the concentration of oxygen-centered free radicals in a sample, comprising:
   combining a working reagent comprising a chromogen and a buffer with a sample containing oxygen-centered free radicals, to form a mixture substantially free of compounds known to complex transition metal ions;
   quantitatively determining the concentration of said oxygen-centered free radicals in said mixture;
   wherein said chromogen has a formula:

wherein $R_1$, $R_2$, $R_3$, and $R_4$ are substituents selected from the group consisting of —$CH_2CH_3$, —$CH_3$, —H, or —X, wherein X is a halogen;
   wherein said buffer has a pH of from 3 to 6.9; and
   wherein said chromogen is dissolved in a suitable solvent to form a solution.

2. The method according to claim 1, wherein said sample is a biological sample.

3. The method according to claim 1, wherein said sample is a nonbiological sample, and wherein said method comprises the additional step of adding a transition-metal ion salt to said mixture after said reagent and said sample are combined, and before said concentration of oxygen-centered free radicals is quantitatively determined.

4. The method according to claim 3, wherein said transition-metal ion salt is a member selected from an iron (II) salt and a cuprous (I) salt.

5. The method according to claim 4, wherein said transition-metal ion salt is iron (II) sulfate.

6. The method according to claim 4, wherein said transition-metal ion salt is cuprous (I) sulfate.

7. The method according to claim 2,
   wherein the volume proportion of said chromogen solution to said buffer is from 1:20 to 1:300.

8. The method according to claim 3,
   wherein the volume proportion of said chromogen solution to said buffer is from 1:20 to 1:300.

9. The method according to claim 2, wherein said chromogen is N,N-diethyl-1,4-phenylenediamine, N,N-dimethyl-1,4-phenylene diamine, or salts thereof.

10. The method according to claim 3, wherein said chromogen is N,N-diethyl-1,4-phenylenediamine, N,N-dimethyl-1,4-phenylene diamine, or salts thereof.

11. The method according to claim 9, wherein said chromogen is selected from the group consisting of N,N-diethyl-1,4-phenylenediamine sulfate, N,N-diethyl-1,4-phenylenediamine oxalate, N,N-dimethyl-1,4-phenylenediamine sulfate, and N,N-dimethyl-1,4-phenylenediamine oxalate.

12. The method according to claim 10, wherein said chromogen is selected from the group consisting of N,N-diethyl-1,4-phenylenediamine sulfate, N,N-diethyl-1,4-phenylenediamine oxalate, N,N-dimethyl-1,4-phenylenediamine sulfate, and N,N-dimethyl-1,4-phenylenediamine oxalate.

13. The method according to claim 2, wherein said buffer has a pH value of from 4 to 5.

14. The method according to claim 3, wherein said buffer has a pH value of from 4 to 5.

15. The method for determining the concentration of oxygen-centered free radicals as defined in claim 2, further comprising:

developing a color of said mixture; and comparing the absorption spectrum of said mixture to a known sample having a predetermined concentration of oxygen-centered free radicals and calculating the concentration of oxygen-centered free radicals in said sample.

16. The method for determining the concentration of oxygen-centered free radicals as defined in claim 3, further comprising:

developing a color of said mixture; and comparing the absorption spectrum of said mixture to a known sample having a predetermined concentration of oxygen-centered free radicals and calculating the concentration of oxygen-centered free radicals in said sample.

17. The method for determining the concentration of oxygen-centered free radicals as defined in claim 2, further comprising:

measuring the initial absorption of said mixture;

measuring the absorption of said mixture after a specified period of time; and comparing the initial absorption and subsequent absorption of said mixture to a known sample having a predetermined concentration of oxygen-centered free radicals and calculating the concentration of oxygen-centered free radicals in said sample.

18. The method for determining the concentration of oxygen-centered free radicals as defined in claim 3, further comprising:

measuring the initial absorption of said mixture;

measuring the absorption of said mixture after a specified period of time; and comparing the initial absorption and subsequent absorption of said mixture to a known sample having a predetermined concentration of oxygen-centered free radicals and calculating the concentration of oxygen-centered free radicals in said sample.

19. The method for determining the concentration of oxygen-centered free radicals as defined in claim 2, further comprising:

measuring the absorption of said mixture over a period of time, wherein said reaction rate is constant; and comparing the absorption of said mixture to a known sample having a predetermined concentration of oxygen-centered free radicals and calculating the concentration of oxygen-centered free radicals in said sample.

20. The method for determining the concentration of oxygen-centered free radicals as defined in claim 3, further comprising:

measuring the absorption of said mixture over a period of time, wherein said reaction rate is constant; and comparing the absorption of said mixture to a known sample having a predetermined concentration of oxygen-centered free radicals and calculating the concentration of oxygen-centered free radicals in said sample.

21. The method according to claim 1, wherein the oxygen-centered free radicals are selected from the group consisting of an oxygen superoxide radical anion, an alkoxy radical, a peroxy radical and a hydroxy radicals.

* * * * *